United States Patent
Taguchi et al.

[11] 4,003,708
[45] Jan. 18, 1977

[54] AUTOMATIC PHOTOMETRIC ANALYZER

[75] Inventors: Isamu Taguchi, Tokyo; Akihiro Ono, Yokohama; Ryutaro Matsumoto, Tokyo, all of Japan

[73] Assignees: Nippon Steel Corporation; Kokusai Electric Co., Ltd., both of Tokyo, Japan

[22] Filed: May 6, 1975

[21] Appl. No.: 575,078

Related U.S. Application Data

[63] Continuation of Ser. No. 511,205, Oct. 2, 1974, abandoned, which is a continuation of Ser. No. 283,851, Aug. 25, 1972.

[30] Foreign Application Priority Data

Aug. 26, 1971    Japan .......................... 46-65729

[52] U.S. Cl. ..................... 23/253 R; 23/230 R
[51] Int. Cl.² ................................ G01N 31/00
[58] Field of Search .................. 23/253 R, 230 R

[56] References Cited
UNITED STATES PATENTS

| | | |
|---|---|---|
| 2,879,141 | 3/1959 | Skeggs .................. 23/253 R |
| 3,690,833 | 9/1972 | Ferrari .................. 23/253 R |
| 3,694,160 | 9/1972 | Sagusa et al. ............ 23/230 R |
| 3,700,562 | 8/1972 | Morgenstern et al. ...... 23/253 R X |
| 3,723,062 | 3/1973 | Dahms ................... 23/253 R X |

Primary Examiner—Norman Yudkoff
Assistant Examiner—Dale Lovercheck
Attorney, Agent, or Firm—Toren, McGeady and Stanger

[57] ABSTRACT

An automatic photometric analyzer is disclosed using an automatic exchanger holding a sample solution. A recorder, a photometer, an injector for the sample solution, and supply systems for pure water and coloring solutions are used. Additionally, valves under control of an automatic controller properly control the flow and the solution to provide a simple and practical apparatus with rapid automatic operation for analysis. The injector delivers reactant solutions to a reactor from which reactant is circulated through the photometric means to measure the absorbency thereof and back to the reactor.

11 Claims, 11 Drawing Figures

FIG. 2

FIG. 3 wave length: 700 mμ
flow cell: 20 mm
reference
 liquid: water

FIG. 4 wave length: 700 mμ
flow cell: 20 mm
reference
 liquid: water

AUTOMATIC PHOTOMETRIC ANALYZER

This is a continuation of Application Ser. No. 511,205 filed Oct. 2, 1974 and now abandoned which is a continuation of Ser. No. 283,851 filed Aug. 25, 1972.

BACKGROUND OF THE INVENTION:

In principle, photometric analysis is a method for determining the quantity of elements in a sample solution in which the solution color is affected and by the elements specific wave lengths are measured.

Since photometric analysis has great advantages over other wet chemical analysis with respect to sensitivity, selectivity, rapidity, etc., much research for analysis methods has been attempted for various kinds of samples.

However, conducting these analyses is complicated and troublesome, requiring much time and expert techniques. The photometric analysis method may be roughly classified into following five unit steps or operations. These operations are:

1. Preliminary treating of sample solution,
2. Adding coloring solutions,
3. Coloration,
4. Measuring for absorbancy and
5. Measuring for a blank value.

In some cases, one or two of the above operations may be omitted, but, in principle, the operations are carried out in the above mentioned order. Quantitative analysis of the elements is calculated from prepared calibration curves.

In case of a solid sample, a dissolving operation is added prior to the operation (1), so that when the solution sample, which is a solution of the solid sample, is used as a starting substance, the operations are the same.

There are two typical types of automatic photometric analysers on the market. One operates as follows: a sample solution and coloring solution are continuously fed by means of a pump, coloring reactions occur in a feed pipe and at the end portion of feed pipe, apparatus is located for continuously measuring the absorbancy. The other type operates as follows: A number of test tubes are successively moved, and a sample solution and coloring solution are successively injected into the test tubes by means of an injection type pump to carry out color reaction. Thus the test tubes are then used as cells for measuring the absorbancy, and the absorbancy of solution in the test tubes may be continuously measured.

However, with regard to simplicity, low cost, precision and accuracy of analysis, these types of apparatus are not sufficient for practical use.

SUMMARY OF THE INVENTION

This invention relates to an automatic method and apparatus of photometric analysis, in which usual complicated and troublesome manual operations are simplified.

The object of this invention is to provide a simple, cheap and practical method and apparatus for simplifying photometric analysis.

According to the invention, this object may be attained by a system which is quite different from those on the market. This system employs novel elements of photometric analysis for better results as to precision and accuracy, compared with that obtained by prior manually operated analysis devices.

DESCRIPTION OF THE PREFERRED EMBODIMENTS

The present invention will be explained in detail with reference to FIG. 1.

1 denotes an automatic exchanger for the sample solution to exchange automatically a number of vessels containing the sample solution. In FIG. 1, a turn table system is diagramatically shown, however, other automatic exchange systems, such as a belt conveyor may be also used. In the exchanger, there is provided a tube connected with an injector 4 for the sample solution and a tube connected with an electromagnetic cock 11, each of the tubes being respectively fixed to elevators of the exchanger. The length of the tip of tube from its fixed position is such that the tip may reach the bottom of the vessel on the exchanger, and a certain portion of the sample solution initially contained in the vessel is fed to the injector 4 by the injector for sample solution. For this feeding, a vacuum suction or pressure feed or the like may be used.

After the sample solution is supplied, an amount of pure water is poured into the vessel from the tube connected with the electromagnetic cock 11 to rinse the vessel, and the solution is fed to the injector 4 again.

2 denotes a recorder.

3 is a photometer, for which any type may be used. In the light passage area of the photometer, there is arranged a flow cell 17. An air blow pipe 18 circulates the solution, but, circulation by means of any small size pump may be used.

4 is an injector for the sample solution and is made of glass. The sample solution fed from the exchanger 1 and pure water which rinsed the vessel is temporarily accumulated in injector 4, and an electromagnetic cock 10 is used to inject a solution from injector 4 into a main reactor body 14.

5 is a three way electromagnetic valve between a vacuum pump and the injector to change the flow passages and make the pressure of the injector for the sample solution to be under vacuum or atmospheric pressure.

6 is a bottle for pure water, and 7 are bottles for coloring solutions. Bottles of about 500 ml to 3 liters are the most suitable.

In the drawing numerals, 8, 10, 11 and 12 are electromagnetic cocks, which are opened and closed under control of an automatic controller 21. The electromagnetic cock 8 is used to supply solution from the bottles 6 and 7 to liquid level controllers 9, and the electromagnetic cock 10 is used to supply a sample solution contained in the sample injector 4 and pure water to the reactor 14. The electromagnetic cock 11 is used to supply pure water for rinsing the sample solution remaining in the sample vessel. The electromagnetic cock 12 is used to supply pure water or coloring solution from the liquid level controller 9 to the reactor 14. 20 is an electromagnetic cock for discharging the waste solution.

The ability to reproduce an addition mechanism by using bottles 6, 7, electromagnetic cocks 8, liquid level controllers 9 and electromagnetic cocks 12 according to the present invention was investigated, the results of which are shown in Table 1 below.

Four sets of the addition mechanism are prepared, by filling all bottles (made of polyethylene, capacity 1 liter) with water. As shown in FIG. 1, then the electromagnetic cock on the lower portion of the liquid level controller was opened for 30 seconds, and water was received by a measuring cylinder through narrow tube on the lower portion of cooling pipe and was measured.

According to the Table 1, the amount of water to be added within 30 seconds is somewhat different for each addition mechanism, however, the reproducibility of addition mechanism is good compared with the case, in which the addition is carried out manually by using a pipet. A cooling tube 13 in FIG. 1 is treated in a portion of the reactor 14 where sample solution and the like is prevented from becoming lost by heating.

Table 1

The reproducibility of added solution due to an addition mechanism (ml, water used)

| Addition mechanism | 1st | 2nd | 3rd | 4th | 5th | Mean |
|---|---|---|---|---|---|---|
| No.1 | 32.1 | 32.0 | 32.0 | 32.0 | 32.2 | 32.1 |
| No.2 | 33.0 | 28.1 | 28.0 | 28.2 | 28.1 | 28.1 |
| No.3 | 33.0 | 33.1 | 32.9 | 33.0 | 33.0 | 33.0 |
| No.4 | 29.5 | 29.5 | 29.5 | 29.7 | 29.6 | 29.6 |

In the portion where the coloring reaction and measurement according to the present invention are carried out (hereinafter called coloring reaction and measuring portion), a temperature control device is provided so that heating by a heater 15 or cooling by water may be effected according to the conditions for coloring.

Figure 1:
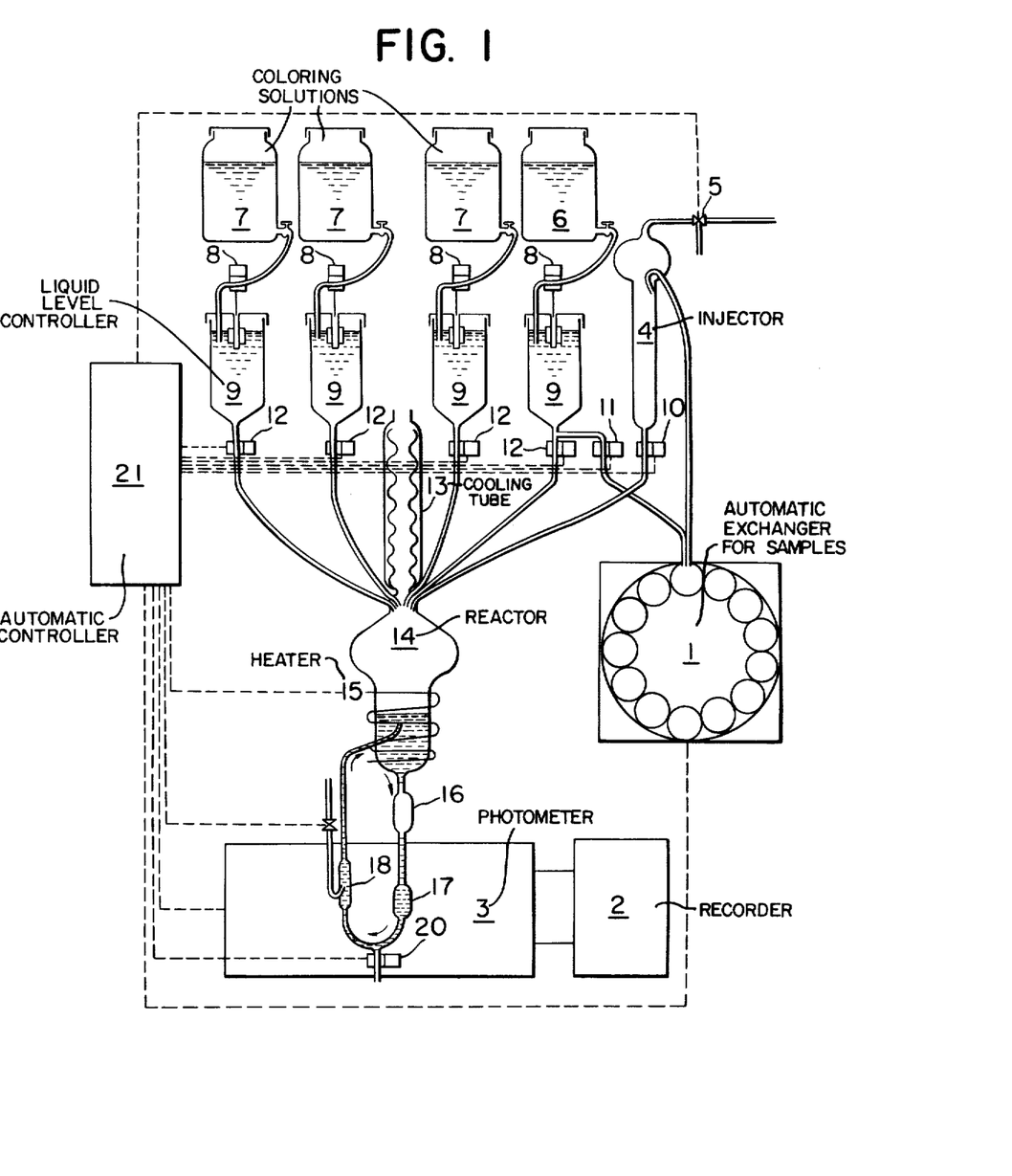
FIG. 1 is an explanatory drawing of apparatus according to the present invention.

As will be seen from FIG. 1, the characteristics of the coloring reaction and measuring portion consists in that a circulation tube starting from the lower portion of the reactor 14 and returning to its central portion is provided, and quantities of sample solution and coloring solution are added for set time periods into the reactor 14. The coloring reaction and coloring solution is circulated by air from the blow pipe and during circulation, bubbles in the circulating solution are removed by means of a bubble-eliminating tube 16 and absorbancy of the solution as to the coloring reaction is measured continuously by a flow cell 17 of a photometer 3.

The function of the coloring reaction portion will be explained in detail hereinafter.

The sample solution injected into the reactor 14 reacts with coloring solutions added afterwards to produce a color; however, this reaction sometimes requires considerable time at room temperature and in some cases it is necessary to keep the temperature constant. Therefore, to accelerate the reaction, a heating device 15 applied to the outer wall or temperature control such as by cooling or by a simple thermostat is achieved. For carrying out a uniform reaction, it is desirable to circulate the solution and stir. The circulation of solution by means of this circulation tube not only assures the stirring action of the solution, but also meets the first object that the mean absorbancy of the solution is continuously measured by the flow cell 17. Thus by using the circulation tube, both the heating effect of the heater on the photometer and the effect of air bubbles generated or mixed in the solution may be removed at the same time. This solution is circulated in the direction of the arrow in FIG. 1, and circulation by an air blow pipe (instead of air, other gases such as an inert gas may be used) having a simple construction is achieved.

In this air blow pipe, an air blow nozzle is directed upwardly and the device is very small in size, simple in construction and low in cost, but nevertheless, rapid circulation of solution may be assured. And, the air blown in by means of this blow pipe presents sudden boiling of solution in case it is heated by the heater in the reactor.

It is possible to replace the air blow pipe construction described above by a pump, however, no such pump of small size, low cost which is also acid proof may be found at present.

It is also a characteristic to attach a bubble eliminating tube 16 to this circulation pipe, wherein the elimination tube is made up merely by enlarging a pipe (having 10 mm dia. lower portion of the reaction pipe) to a diameter of about twice the prior size. Bubbles mixed in the solution by the circulation mixing and bubbles generated by heating are completely removed within the elimination tube and never reach the flow cell, so that the measurement of absorbancy will not be disturbed.

21 in FIG. 1 denotes an automatic controller.

Although a detailed explanation is given above for the photometric analyser according to the present invention, further characteristics of the analyser are that a number of sample solutions are mounted on the automatic exchanger 1 in FIG. 1, while all of other analysis operations are automatically carried out by means of the automatic controller 21 to record the results of the analysis.

In the analyser according to the present invention, the change of the absorbency with respect to time is recorded, the results of which may be digitally typed out by using a computer, As shown by the dotted lines in FIG. 1, the automatic controller 21 is connected with the sample solution automatic exchanger 1, photometer 3, three way electromagnetic valve 5, electromagnetic cocks 10, 11, 12, heater 15, electromagnetic valve 19 and electromagnetic cocks 20 and automatically controls the exchange of sample solution, suction to the injector for sample solution, addition of sample solution to the reactor, injection of pure rinsing water into the vessel filled with the sample solution, addition of pure water and coloring solution to the reactor, heating, blow-in of the air to the circulation pipe, and the discharge of water, etc.

In this analyser, a program timer of the rotary drum system is used as the automatic controller, however, all of conventional program timers, for example, pinboard system and Seakens programmer may be also used. The programs will be mentioned in detail in the following examples, however, they are determined experimentally for every constituent and sample to be analysed.

EXAMPLE 1

Phosphorus analysis

Figure 2:
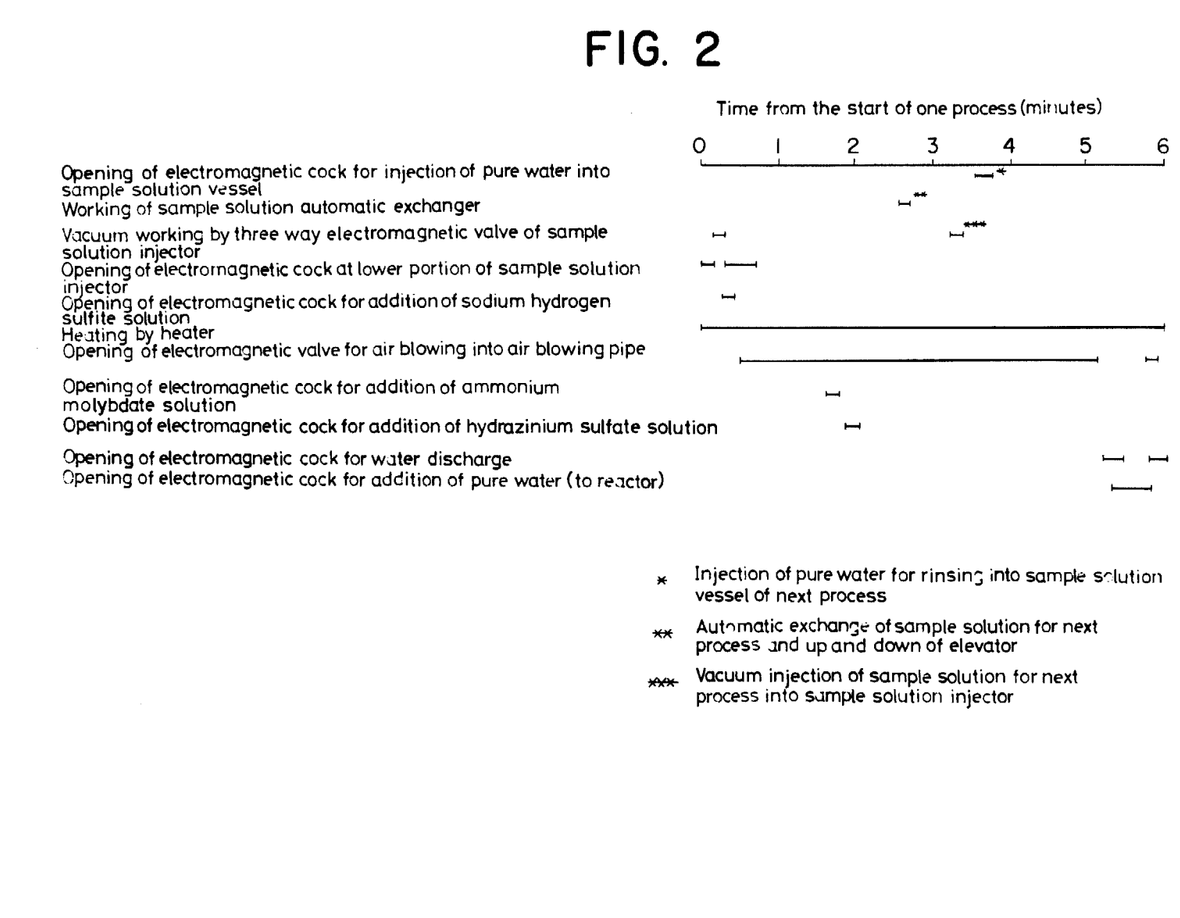
FIG. 2 is a method for analysis of phosphorus by means of the apparatus according to the present invention.

There are a number of photometric analytical methods for phosphorus, however, most of them are carried out by hydrazin sulfate reduction molybdenum blue. To carry out phosphorus analysis by this method, three bottles are used for the coloring solution. Three kinds of solution are placed in the bottles respectively. These are sodium hydrogen sulfite solution (20%), ammonium molybdate solution (25 g of ammonium molybdate is dissolved in 375 ml of sulfuric acid and 1 liter of water, and diluted with water, and hydrazin sulfate solution (0.15%). All of other apparatus are those explained above in FIG. 1. As shown in FIG. 2, an analysis program or method is made as one process for a total of six minutes.

FIG. 2 shows how the respective automatic control is practiced. This program is made by determining the optimum analysis conditions from the results of fundamental experiments of phosphorus analysis according to the present invention.

Figure 3:
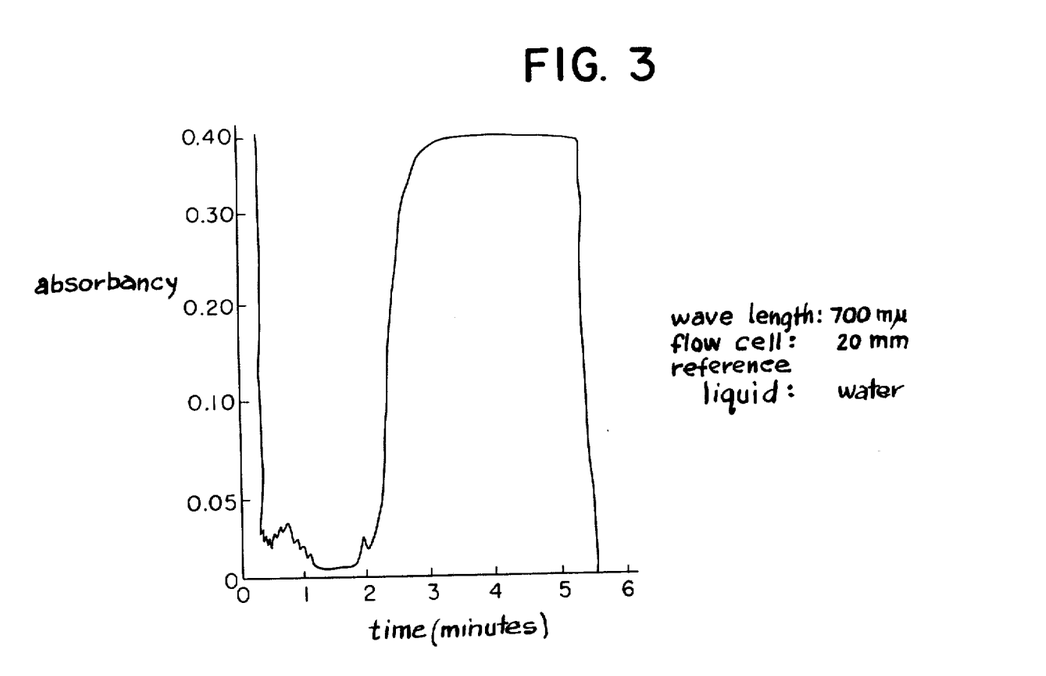
FIG. 3 is a diagram showing the relationship between absorbancy and time found in the apparatus according to the present invention.

In FIG. 3, a chart is presented of the time change of absorbancy within six minutes of one process which is recorded, by using phosphorus solution, according to the program of FIG. 2. The apparatus according to the present invention is used to practice this method of FIG. 2, and FIG. 3 is explained hereinafter.

As mentioned above, the sample solution and pure water after rinsing are injected into the reactor and the solution enters into the lower portion of the reactor and the circulation pipe. During this injection, step sodium and reactant are electrically heated.

After the addition step of sodium hydrogen sulfite solution is finished, the air blowing into the pipe is started and the circulation of the solution begins.

With time lapse, the absorbancy becomes nearly stable. This stable absorbancy is attributable to the added sodium hydrogen sulfite solution, and if any colored ion such as nickel ion and chromium ion, etc. is contained in large quantity, the absorbancy will become stronger. Since this absorbancy is not attributed to the phosphorus which being the object of measure, it must be deducted from the measured value and is the so-called blank value. The blank value to be deducted from this measured value should be corrected from the quantity of solution at the time of measurement and of the finally measured value. In succession, as seen from FIG. 2, ammonium molybdate solution and hydrazin sulfate solution are added. After a time, the formation of molybdenum blue occurs, the absorbancy increases and becomes constant after about three minutes from the beginning. Conservatively, absorbancy is measured at about five minutes. Thereafter, the discharge of the liquid and the rinsing operations of the reactor and of the inside wall of the circulation pipe occurs.

Figure 4:
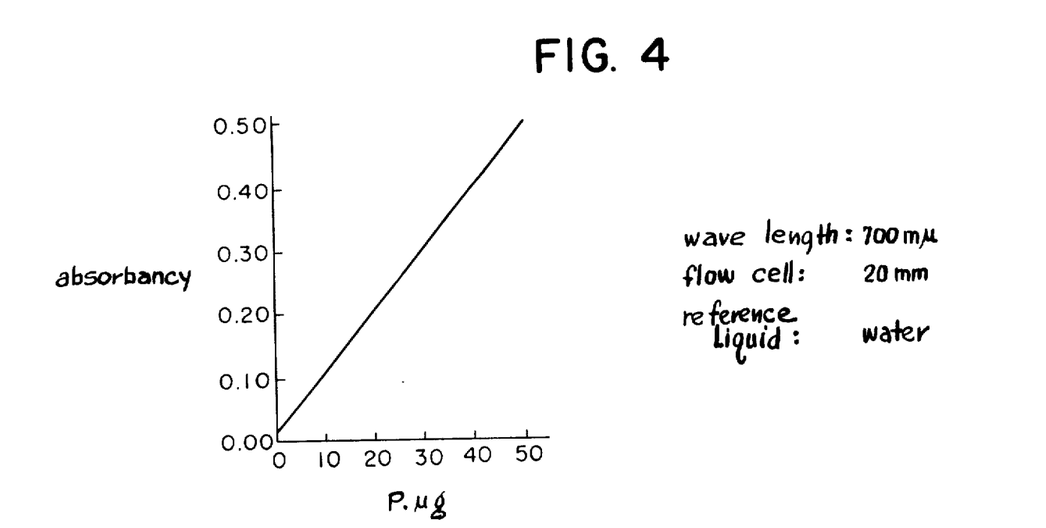
FIG. 4 is a diagram showing an example of a calibration curve for phosphorus by means of the same apparatus.

According to the present apparatus and the program of FIG. 2, various solutions which are stepwisely added with standard phosphorus solution are subject to the coloring reaction, measuring the absorbancy, making the calibration curve for phosphorus analysis according to the present apparatus, and the result thereof is shown in FIG. 4. It has been proved that the calibration curve of FIG. 4 has good linearity and is sufficiently practical. When 0.1 g of iron coexists as an ion in the solution, the calibration curve was not changed. According to the calibration curve, the phosphorus analysis was made for a steel sample (the analysis was carried out after making a sample solution by decomposition with acid), of which the results were compared with the results of phosphorus analysis carried by the manually operated molybdenum blue absorbancy method and is shown in Table 2.

Table 2

Comparison of phosphorus analysis (%) in steel sample according to the apparatus of the present invention and prior method.

| Name of sample | Results by the present apparatus | Results by manual operation |
|---|---|---|
| No.1 | 0.011 | 0.011 |
| No.2 | 0.021 | 0.021 |
| No.3 | 0.037 | 0.037 |
| No.4 | 0.003 | 0.003 |
| No.5 | 0.024 | 0.024 |
| No.6 | 0.115 | 0.114 |
| No.7 | 0.040 | 0.039 |
| No.8 | 0.045 | 0.045 |

According to Table 2, it has been proved that the analysis by the present apparatus compares well with that of the manual operation.

The phosphorus analysis by prior manual operation takes about 40 minutes for one process, while the phosphorus analyis by the apparatus according to the present invention takes only 6 minutes and because of automatic operation, no special skill is required therefor.

EXAMPLE 2

Manganese analysis

In the following explanation, those parts overlapping with the explanation in Example 1 will be omitted. There are a number of photometric analyses methods available for manganese, however, most of them are analyzed by the periodic acid oxidation photometric method. To carry out manganese analysis by this method, two bottles of coloring solution are used and two kinds of solution are placed therein respectively. These are urea (5%) - silver nitrate (2%) solution and sodium periodate solution (5%). The apparatus in FIG. 1 is employed. Analysis program is set forth in FIG. 5 and one process takes 6 minutes.

Figure 5:
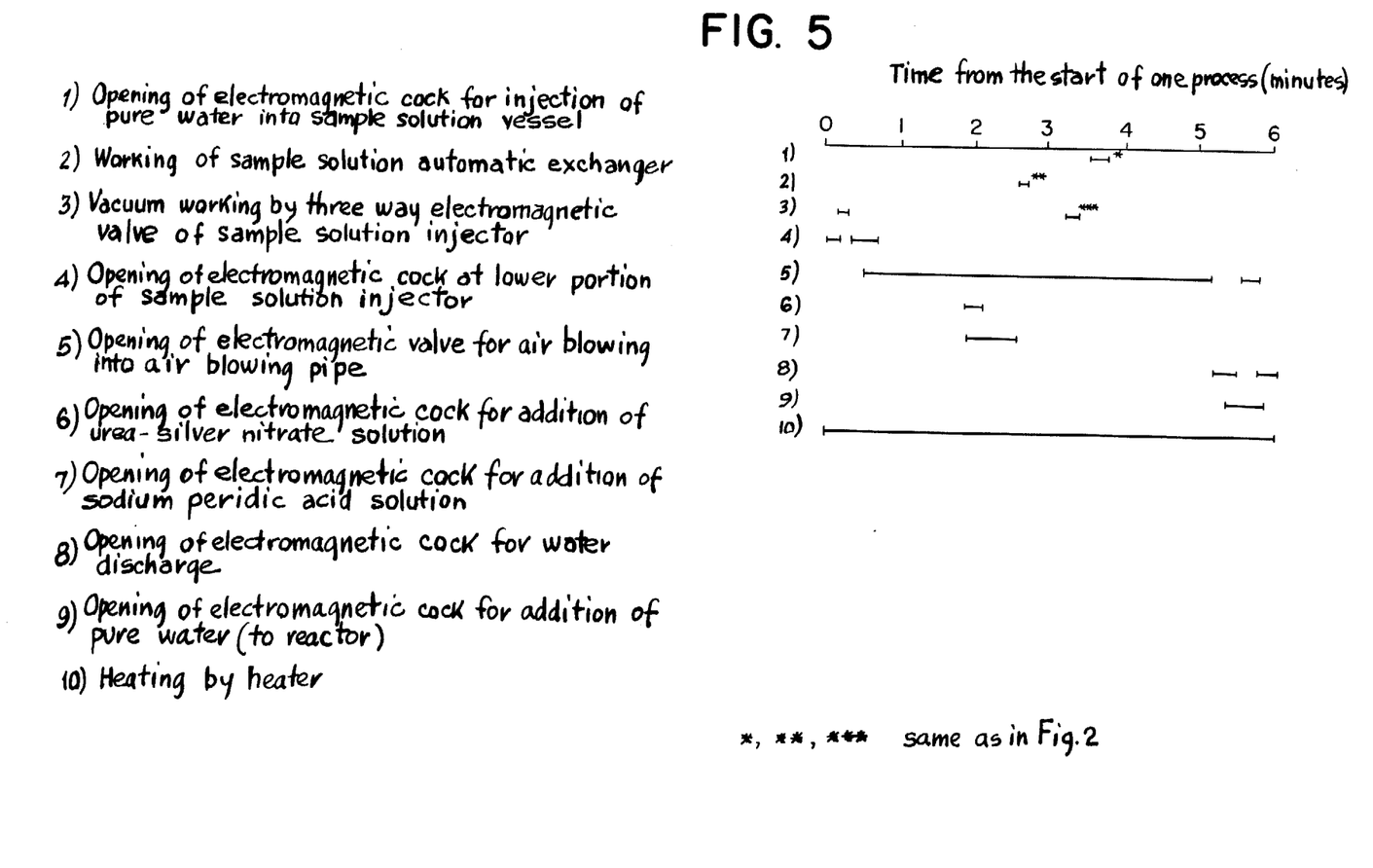
FIG. 5 is a method for analysis of manganese by means of the apparatus according to the present invention.

By means of the present apparatus, according to the program of FIG. 5, and by using manganese solution (quantity of manganese: 500 µg) the change of absorbancy with time within 6 minutes for one process was recorded. The results were similar to the case of FIG. 3 of Example 1, and the absorbancy of the solution became constant after about 2 minutes and 40 seconds after one process was started. However, when chromium ion and the like are coexist in the sample solution, coloring will be delayed, so that for safety the measuring value was obtained after 5 minutes elapsed after one process was started. The blank value is corrected prior to the measuring of the value in the range of one to one half minutes after starting, when the absorbancy become constant, similarly to Example 1.

Figure 6:
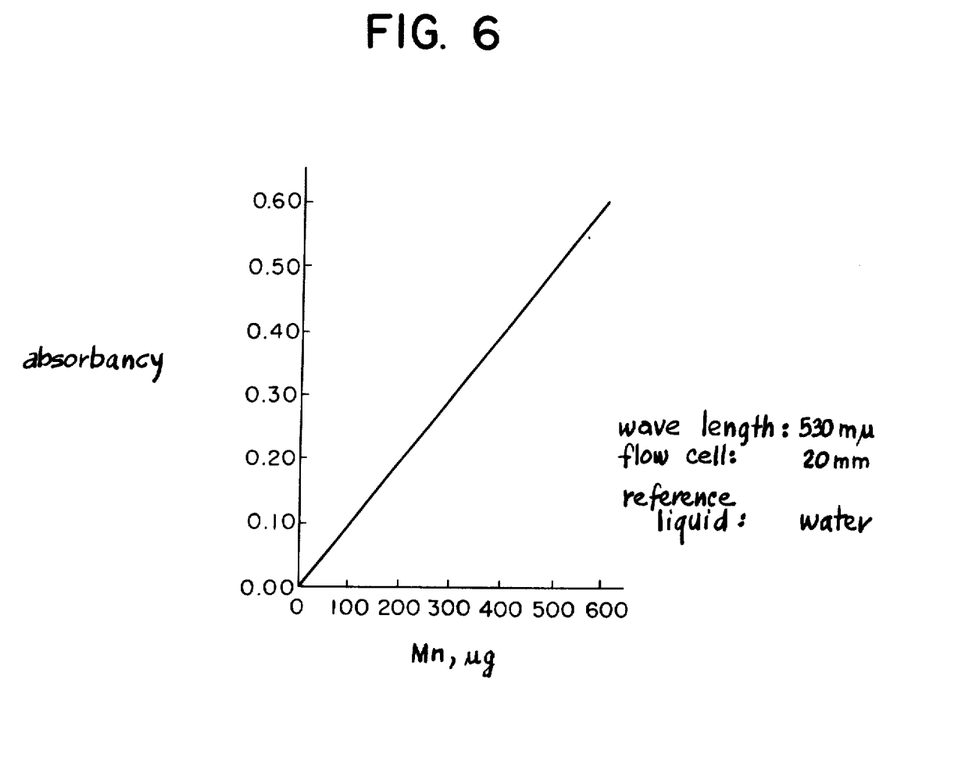
FIG. 6 is a diagram showing an example of a calibration curve for manganese by means of the same apparatus.

A calibration curve made for standard manganese solution, according to the present apparatus and the program of FIG. 5, and is shown in FIG. 6. It has been proved that the calibration curve of FIG. 6 has good linearity and is sufficiently practical. By means of the present apparatus and according to the program in FIG. 7 and the calibration curve of FIG. 6, manganese in a river water sample is analysed, of which the results are shown in Table 3, which are compared with the results of manual analysis by the periodic acid oxidation photometric method.

Table 3

Results of analysis of manganese in river water (ppm) by means of the apparatus according to the present invention compared with the periodic acid oxidation phetometric method.

| Name of sample | Results by means of the present apparatus | Results by manual operation |
| --- | --- | --- |
| No.1 | 0.10 | 0.10 |
| No.2 | 0.23 | 0.22 |
| No.3 | 0.05 | 0.06 |
| No.4 | 0.07 | 0.07 |
| No.5 | 0.18 | 0.18 |
| No.6 | 0.21 | 0.21 |

According to the results of Table 3, it is seen that the results of analysis by means of the present apparatus closely coincides with that of manual operation.

The manganese analysis by the manual operation process takes about 30 minutes for one process, while the manganese analysis by the apparatus according to the present invention takes only 6 minutes and because of the automatic operation, no special skill is required therefor.

EXAMPLE 3

Aluminum analysis

Analysis by means of the apparatus for microaluminum in a sample solution will be described, as follows, however, those parts overlapping with the explanation in Examples 1 and 2 above will be omitted. There are a number of photometric analyses for microaluminum, however, most of them are analyzed by the eriochromecyanin R photometric method. To determine aluminum by this method, three bottles of coloring solution are used and three kinds of solution placed therein, respectively. These are thioglycollic acid solution (3%), eriochromecyanin R solution (0.05%) and polycyclic keto-amin solution (320 g of ammonium acetate and 20 g of sodium sulfite are dissolved in 1 liter of water and 3 ml of polycyclic keto-amin is added and stirred up). Others are same as those explained in FIG. 1. The analysis program is determined as in FIG. 7 and one process is set to take 6 minutes.

Two items are to be mentioned specially, as compared with Examples 1 and 2. One is that in Examples 1, 2, the circulation of the solution was carried out by blowing the air into the pipe, while in this example for aluminum analysis, the air is replaced by nitrogen. As mentioned above, the program of FIG. 7 is made from the results of fundamental examination of aluminum analysis by means of the present apparatus. However, it was seen that when iron ion coexisted in the sample solution, the ion was oxidized by the air and iron trivalent ion is produced, resulting in an analytical error, so that the air was replaced by nitrogen, which is inert gas. In such a manner, it is very easy with the apparatus shown in FIG. 1 to make the reactor and the inside of the circulation pipe into an atmosphere of inert gas, which may be considered as one feature of the present apparatus, which compared with the manually operating analysis, in which it is very difficult to carry out the coloring reaction in an atmosphere of inert gas.

The other special matter is that in the eriochromecyanin R photometric method, it takes a long time for perfect coloring, and therefore constant absorbancy is not easily obtained causing analytical error to occur by manual anaylsis. By means of the present apparatus, the absorbancy after a constant time from the start of analysis of one process may be measured, so that a correct analysis may be carried out without any analytical error. The above matters will be explained in further detail from FIG. 8, wherein the time change of absorbancy of aluminum according to the program of FIG. 7 by means of the present apparatus is shown.

Figure 8:
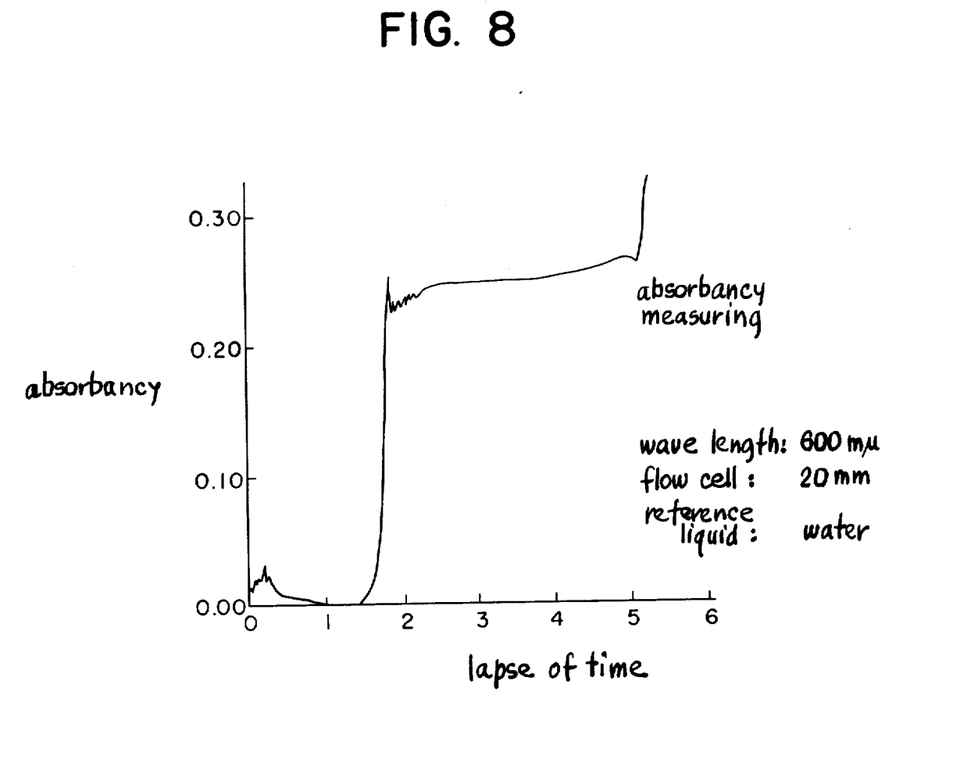
FIG. 8 is a record chart of time change of absorbancy (in case of aluminum analysis) by means of the apparatus according to the present invention.

The reaction among aluminum, eriochromecyanin R solution and polycyclic keto-amin solution is slow, and even after 5 minutes from the start of analysis of one process, the absorbancy is raised higher, as seen from FIG. 8. Therefore, it has been prepared so that the solution is discharged after 5 minutes and 5 seconds from the start of analysis of one process, thus the absorbancy of the solution is read just before that time. When the reproducibility of the measured value of the absorbancy is examined, it is seen that the property of reproducibility is very good and sufficiently practical. The usual analysis carried out by manual operation is based on the premise of perfect coloring of the sample solution and coloring solution and methods have been developed therefor. Nevertheless, for some analytical constituents, no coloring solution and methods have been found to the present. Therefore, by means of the present apparatus, the constituent may be analysed even though it is not always perfectly reacted with coloring solution, this point deserving special mention.

Figure 7:
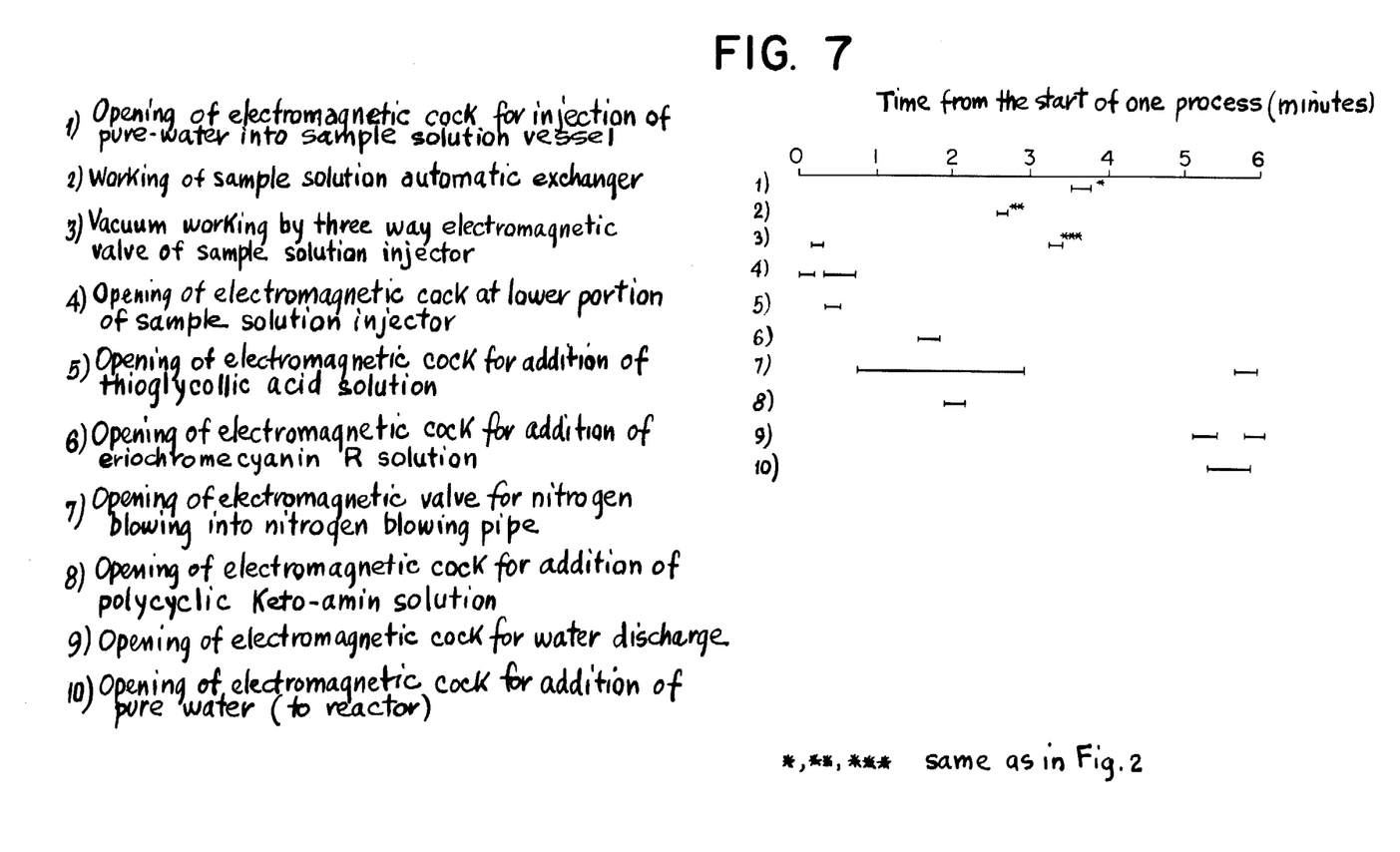
FIG. 7 is a method for analysis of aluminum by means of the apparatus according to the present invention.
Figure 9:
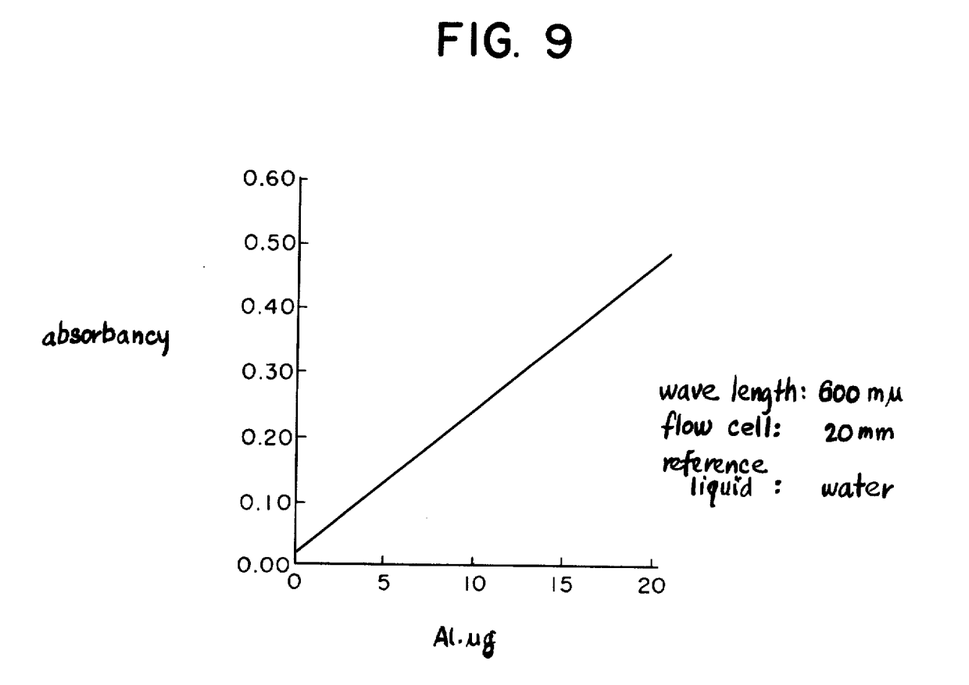
FIG. 9 is a diagram showing an example of a calibration curve for aluminum by means of the same apparatus.
Figure 10:
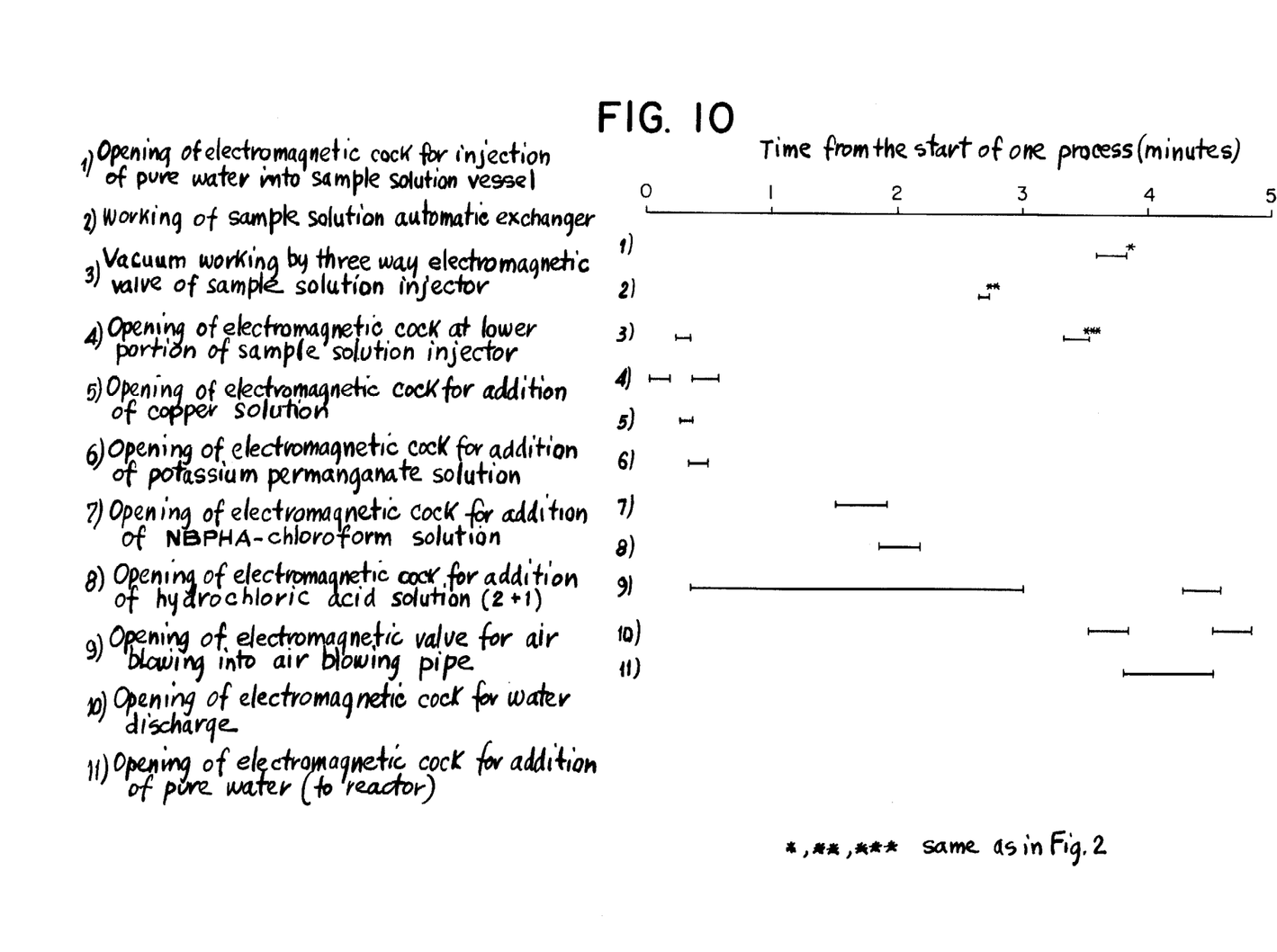
Figure 11:
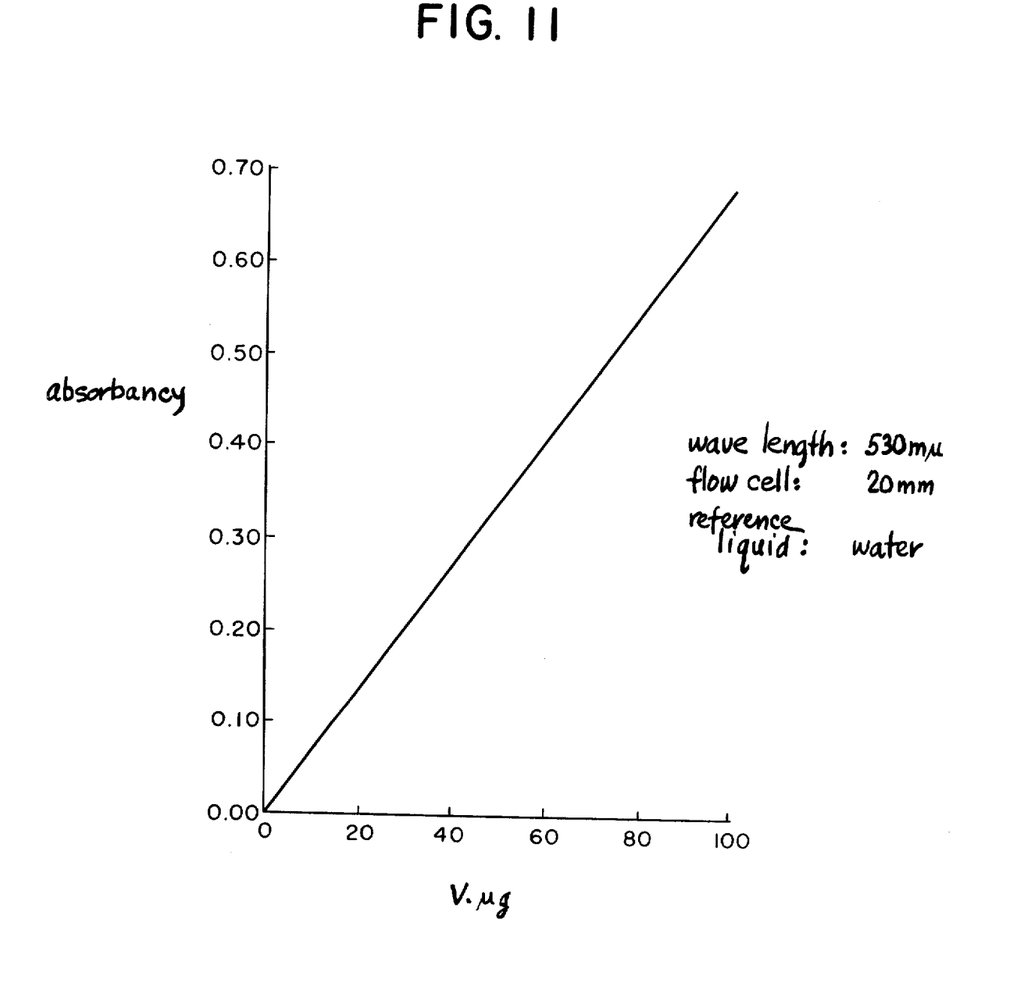

According to the present apparatus and the program of FIG. 7, various water solutions stepwisely added with standard aluminum solution is colorized, and the absorbancy is measured. A calibration curve for aluminum analysis by means of the present apparatus is made as shown in FIG. 9. It has been proved that the calibration curve of FIG. 9 has good linearity and is sufficiently practical. By means of the present apparatus and according to the program of FIG. 7 and the calibration curve of FIG. 9, aluminum in a city water sample is analyzed, the results of which are shown in Table 4 in comparison with that of an analysis by the manually operated Eriochromecyanin R photometric method.

Table 4

Comparison of results of analysis of aluminum in city water (ppm) by means of the apparatus according to the present invention and prior art manually operated Eriochromecyanin R photometric method.

| Name of sample | Results by means of the present apparatus | Results by manual operation |
| --- | --- | --- |
| No.1 | 0.08 | 0.08 |
| No.2 | 0.02 | 0.02 |
| No.3 | <0.01 | <0.01 |
| No.4 | 0.03 | 0.03 |
| No.5 | 0.03 | 0.02 |
| No.6 | 0.09 | 0.09 |
| No.7 | 0.02 | 0.02 |

Table 4-continued

Comparison of results of analysis of aluminum in city water (ppm) by means of the apparatus according to the present invention and prior art manually operated Eriochromecyanin R photometric method.

| Name of sample | Results by means of the present apparatus | Results by manual operation |
|---|---|---|
| No.8 | 0.07 | 0.07 |

According to the results of Table 4, it is seen that the results of analysis by means of the present apparatus coincided closely with that of a manual operation and is sufficiently correct and practical.

The aluminum analysis by manual operation take about 40 minutes for one process, while the aluminum analysis by the apparatus according to the present invention takes only 6 minutes and because of the automatic operation, no special skill is required.

We claim:

1. An automatic photometric analyzer, comprising an automatic exchanger having a vessel and carrying solutions to be analyzed, a reactor, injector means for injecting a sample solution from said vessel to said reactor, water supply means, coloring solution supply means, means for controlling the supply of said water and coloring solution to said reactor to form a reactant with said sample solution, photometric analysis means, for measuring the absorbency of the reactant, and fluid passage means coupled to said reactor for circulating said reactant from the reactor through the photometric means and back to the reactor.

2. Apparatus as set forth in claim 1, comprising valve means connected between said water supply means and the vessel of said exchanger for allowing water to wash the vessel from which the sample solution analyzed was taken.

3. Apparatus as set forth in claim 1, comprising liquid level means connected between said water supply means and said reactor and said coloring solution supply means and said reactor for receiving said water and coloring solution respectively.

4. Apparatus as set forth in claim 1, comprising first valve means connected between said water supply means and said reactor for allowing the water to wash said reactor when the absorbency measurements of each sample solution are completed.

5. Apparatus as set forth in claim 1, comprising cooling means for cooling said sample solution in said reactor.

6. Apparatus as set forth in claim 1, comprising means for heating the solution in the reactor.

7. Apparatus as set forth in claim 2, wherein said enlarged section is enlarged to twice the diameter of the average size of said tube means.

8. Apparatus as set forth in claim 2, comprising recorder means connected to said photometric analysis means for recording the analysis.

9. Apparatus as set forth in claim 2, comprising bubble eliminating means connected to said reactor for eliminating bubbles in said circulating system.

10. Apparatus as set forth in claim 9, further comprising tube means connected to said reactor to carry said reactant, said bubble eliminating means comprising an enlarged tubular section of said tube means.

11. An automatic photometric batch analyzer, comprising an automatic exchanger having a vessel and carrying solutions to be analyzed, a reactor having a chamber for holding liquids, injector means communicating between said exchanger and said reactor for injecting a sample solution from said vessel to the chamber of said reactor, water supply means for holding a supply of water, a plurality of coloring solution supply means each for holding a coloring solution, flow means communicating between said water supply means and said chamber and between each of said coloring solution supply means and said chamber for passing liquid from said water supply means and said coloring solution supply means to said chamber, control means coupled to said flow means for selectively controlling the communication between said supply means and said chamber of said reactor on the basis of a particular analysis to be performed so as to form a reactant of selected coloring solutions and water with said sample solution in the chamber, and photometric analysis means communicating with the chamber in said reactor for measuring the absorbency of the reactant said reactor including conduit means communicating with the chamber for circulating the reactant from the chamber through the photometric means and back to the chamber.

* * * * *